(12) United States Patent
Geibel et al.

(10) Patent No.: US 8,784,505 B2
(45) Date of Patent: Jul. 22, 2014

(54) 1-HEXZL-1H-PYRAZOLE-4,5-DIAMINE HEMISULFATE, AND ITS USE IN DYEING COMPOSITIONS

(71) Applicant: The Procter & Gamble Company, Cincinnati, OH (US)

(72) Inventors: Wolfram Geibel, Huenfeld (DE); Ingo Weber, Gruenstadt (DE); Armin Osan, Bebra (DE); Markus Speckbacher, Mettenheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/768,570

(22) Filed: Feb. 15, 2013

(65) Prior Publication Data

US 2013/0212810 A1   Aug. 22, 2013

(30) Foreign Application Priority Data

Feb. 16, 2012   (EP) .................................... 12155709

(51) Int. Cl.
*A61Q 5/10* (2006.01)
(52) U.S. Cl.
USPC ................. 8/405; 8/406; 8/410; 8/423; 8/435
(58) Field of Classification Search
USPC ...................... 8/405, 406, 408, 410, 423, 435
See application file for complete search history.

(56) References Cited

U.S. PATENT DOCUMENTS

| 3,709,437 | A | 1/1973 | Wright |
| 3,937,364 | A | 2/1976 | Wright |
| 4,022,351 | A | 5/1977 | Wright |
| 4,147,306 | A | 4/1979 | Bennett |
| 4,184,615 | A | 1/1980 | Wright |
| 4,615,467 | A | 10/1986 | Grogan |
| 5,061,289 | A | 10/1991 | Clausen |

(Continued)

FOREIGN PATENT DOCUMENTS

| CA | 2646867 A1 | 3/2009 |
| DE | 3432983 A1 | 4/1985 |

(Continued)

OTHER PUBLICATIONS

English Translation of the Patent WO 2005/023209 A1 dated Aug. 16, 2013.*

(Continued)

*Primary Examiner* — Eisa Elhilo
(74) *Attorney, Agent, or Firm* — James T. Fondriest

(57) ABSTRACT

1-hexyl-1H-pyrazole-4,5-diamine hemisulfate, as represented in formula (IX-a), and its use in oxidative dyeing composition. This pyrazole salt was found to combine good stability as raw material and good shade intensity with a range of common couplers when formulated in hair dyeing composition.

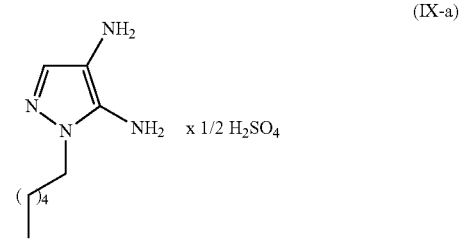

4 Claims, 2 Drawing Sheets

(56) References Cited

U.S. PATENT DOCUMENTS

| | | |
|---|---|---|
| 5,380,340 A | 1/1995 | Neunhoeffer |
| 5,430,159 A | 7/1995 | Neunhoeffer |
| 5,443,569 A | 8/1995 | Uehira |
| 5,534,267 A | 7/1996 | Neunhoeffer |
| 5,663,366 A | 9/1997 | Neunhoeffer |
| 5,718,731 A | 2/1998 | Loewe |
| 5,752,983 A | 5/1998 | Audousset |
| 5,766,576 A | 6/1998 | Loewe |
| 5,769,902 A | 6/1998 | Samain |
| 5,785,717 A | 7/1998 | Maubru |
| 5,865,855 A | 2/1999 | Doehling |
| 5,931,973 A | 8/1999 | Malle |
| 6,053,364 A | 4/2000 | Van der Heijden |
| 6,090,162 A | 7/2000 | Maubru |
| 6,099,592 A | 8/2000 | Vidal |
| 6,118,008 A | 9/2000 | Malle |
| 6,338,741 B1 | 1/2002 | Vidal |
| 6,379,396 B1 | 4/2002 | Audousset |
| 6,452,019 B1 | 9/2002 | Cook |
| 6,503,282 B1 | 1/2003 | Braun |
| 6,554,871 B2 | 4/2003 | Braun |
| 6,600,050 B2 | 7/2003 | Chassot |
| 6,604,693 B2 | 8/2003 | Santagiuliana |
| 6,645,258 B2 | 11/2003 | Vidal |
| 6,660,046 B1 | 12/2003 | Terranova |
| 6,716,257 B2 | 4/2004 | Goettel |
| 6,740,127 B2 | 5/2004 | Friess |
| 6,780,203 B1 | 8/2004 | Maubru |
| 6,793,687 B2 | 9/2004 | Javet |
| 6,855,827 B2 | 2/2005 | Vidal |
| 6,887,280 B2 | 5/2005 | Lim |
| 6,905,522 B2 | 6/2005 | Kravtchenko |
| 6,939,382 B2 | 9/2005 | Fessmann |
| 7,004,979 B2 | 2/2006 | Kravtchenko |
| 7,014,663 B2 | 3/2006 | Fessmann |
| 7,018,426 B2 | 3/2006 | Javet |
| 7,056,354 B2 | 6/2006 | Fessmann |
| 7,070,629 B2 | 7/2006 | Kravtchenko |
| 7,091,350 B2 | 8/2006 | Fessmann |
| 7,153,330 B2 | 12/2006 | Cotteret |
| 7,195,649 B2 | 3/2007 | Goettel |
| 7,250,063 B2 | 7/2007 | Fessmann |
| 7,285,136 B2 | 10/2007 | Fessmann |
| 7,285,137 B2 | 10/2007 | Vidal |
| 7,300,469 B2 | 11/2007 | Fessmann |
| 7,927,381 B2 | 4/2011 | Hercouet |
| 2003/0000027 A1 | 1/2003 | Hoeffkes |
| 2003/0106167 A1 | 6/2003 | Rose |
| 2004/0216242 A1 | 11/2004 | Kravtchenko |
| 2006/0183781 A1 | 8/2006 | Goettel |
| 2006/0219738 A1 | 10/2006 | Izuka |
| 2007/0033742 A1 | 2/2007 | Goettel |
| 2007/0037987 A1 | 2/2007 | Chamberlin |
| 2007/0050924 A1 | 3/2007 | Cotteret |
| 2008/0141468 A1 | 6/2008 | Cotteret |
| 2013/0217891 A1 | 8/2013 | Geibel |

FOREIGN PATENT DOCUMENTS

| | | | |
|---|---|---|---|
| DE | 19619112 A1 | 11/1997 | |
| DE | 10032135 A1 | 1/2002 | |
| DE | 20017640 U1 | 2/2002 | |
| EP | 0663204 A1 | 7/1995 | |
| EP | 0873109 B1 | 2/2004 | |
| EP | 1405628 A1 | 4/2004 | |
| EP | 1488783 B1 | 11/2006 | |
| EP | 1787631 A1 | 5/2007 | |
| EP | 1787632 A1 | 5/2007 | |
| EP | 1795178 A2 | 6/2007 | |
| EP | 1795179 A1 | 6/2007 | |
| EP | 1797863 A1 | 6/2007 | |
| EP | 1985282 A2 | 10/2008 | |
| FR | 2604622 B1 | 12/1990 | |
| FR | 2831055 B1 | 5/2004 | |
| WO | WO0147475 A2 | 7/2001 | |
| WO | WO0209662 A2 | 2/2002 | |
| WO | WO0255500 A1 | 7/2002 | |
| WO | WO02083090 A2 | 10/2002 | |
| WO | WO2004024109 A1 | 3/2004 | |
| WO | WO 2005/023209 A1 * | 3/2005 | ............ A61K 7/13 |
| WO | WO2005023209 A1 | 3/2005 | |
| WO | WO2008047210 A2 | 4/2008 | |
| WO | WO2009077390 A2 | 6/2009 | |

OTHER PUBLICATIONS

STIC Search Report dated Jul. 25, 2013.*

Hans Höhn; XP-002681362; Journal "Zeitschrift für Chemie", 10(10), 386-8; 1970.

* cited by examiner

1-HEXZL-1H-PYRAZOLE-4,5-DIAMINE HEMISULFATE, AND ITS USE IN DYEING COMPOSITIONS

FIELD OF THE INVENTION

The present invention relates to the compound 1-hexyl-1H-pyrazole-4,5-diamine hemisulfate as well as to its use in compositions for the oxidative dyeing of keratin fibers, in particular hair.

BACKGROUND OF THE INVENTION

The oxidative dyeing of hair is one of the most extensively used methods to color hair. In this process, oxidative hair coloring precursors are used in combination with an oxidizing agent, commonly a peroxy oxidizing agent. The oxidative hair coloring precursors are commonly classified into two subclasses; i.e. primary intermediates and couplers. The precursors are generally small molecules capable of diffusing into hair. Another common feature of these precursors is that they mostly contain groups such as amino groups. The presence of these groups is essential to enable the chemistry associated with the oxidative hair dyeing.

While on one hand these amino groups need to be present in the chemical skeleton of the hair coloring precursors to allow the oxidative hair dyeing chemistry to occur, on the other hand one of the drawbacks is that the hair coloring precursors are relatively unstable and degrade over time, especially when exposed under light, humid environment and air. The main degradation products seem to be the oxidized derivatives of these precursors and dimeres thereof.

As known in the hair dyeing field, the oxidative hair dyeing products may be sold in a kit comprising different components to be mixed by the consumer or salon stylist to obtain the desired hair dyeing composition. This kit comprises a so-called tint component comprising the hair coloring dye precursors along with the so-called developer component comprising an oxidizing agent. From the time the hair coloring precursors is manufactured, packed, transported and stored until the material is introduced into the hair dye formulation a long period can lapse. During this period, it has been shown that degradation of the hair dyeing precursors can occur. It has been noticed that the longer these precursors were stored, the higher was the amount of degradation products, in particular oxidized derivatives of these precursors and dimers thereof.

A way to decrease the rate of degradation of the hair dye coloring precursors is to transform them into their corresponding salts in order to maintain these compounds in a reasonably stable stage up to the moment they will be formulated in the tint component. Although more stability on storage can be reached by using the salts of the hair coloring precursors, these salts derivatives may, however, have an impact on the hair dyeing performance.

4,5-diaminopyrazole derivatives are commonly used in the oxidative hair dyeing area due to their good performance as primary intermediates. They give varied shades when mixed with couplers in an oxidative hair dyeing medium.

U.S. Pat. No. 5,663,366 discloses a process for producing 4,5-diaminopyrazole derivatives of the general formula (A):

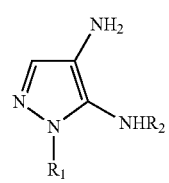

(A)

where $R_1$ and $R_2$ independently designate hydrogen, a $C_1$- to $C_6$-alkyl radical or a $C_2$- to $C_4$-hydroxyalkyl radical, which can be used as dye precursors, for example for hair dyes. The examples describe the process leading to the synthesis of 4,5-diaminopyrazole hydrosulfate, hydrosulfate hydrate and dihydrochloride salts derivatives.

U.S. Pat. No. 7,018,426 discloses an agent for the oxidative dyeing of keratin fibers, wherein it contains (a) at least one 4,5-diaminopyrazole derivative of formula (B), (C), (D) or its salts with organic or inorganic acids as well as (b) at least one resorcinol derivative of the general formula (E), wherein $R_1$ and $R_2$ independently of one another represent hydrogen, a linear or branched $C_1$-$C_6$ alkyl group, an optionally substituted phenyl group or a linear or branched $C_2$-$C_4$-hydroxyalkyl group.

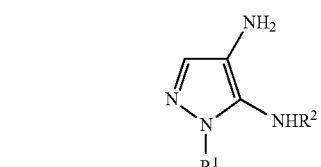

(B)

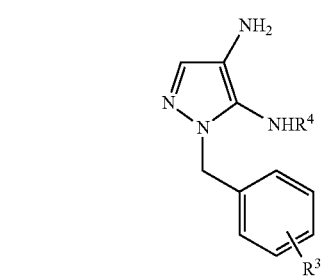

(C)

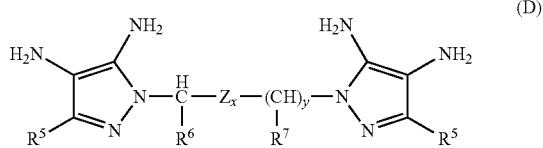

(D)

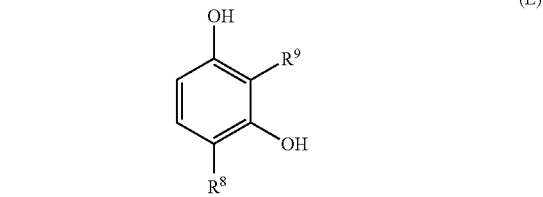

(E)

The examples disclose sulfate, hemisulfate, tetrachloride and dihydrochloride salts of 4,5-diaminopyrazole compounds but not 1-Hexyl-1H-pyrazole-4,5-diamine hemisulfate.

There is a constant need to find primary intermediates which provide good hair dyeing performance as well as good stability during storage, especially in terms of stability over exposure under light, humidity and air.

The invention relates to a novel primary intermediate 1-hexyl-1H-pyrazole-4,5-diamine hemisulfate, which was found to combine a very good stability profile during storage as well as providing the desired colour shade with excellent color intensity.

SUMMARY OF THE INVENTION

The present invention relates to 1-hexyl-1H-pyrazole-4,5-diamine hemisulfate (i.e. the hemisulfate salt of 1-hexyl-1H-pyrazole-4,5-diamine), which can be represented by formula (IX-a).

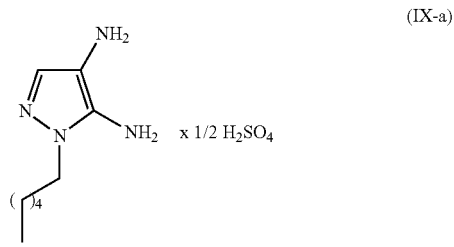

The present invention also relates to a composition for the oxidative dyeing of keratin fibers, in particular human keratin fibers, comprising at least (A) 1-hexyl-1H-pyrazole-4,5-diamine hemisulfate of formula (I), (B) a coupler as defined hereafter, and (C) an oxidizing agent.

Furthermore, the present invention also relates to a method of dyeing hair comprising the steps of applying this composition to hair, and to a kit comprising: (i) a tint component comprising at least (a) a 1-hexyl-1H-pyrazole-4,5-diamine hemisulfate of formula (I) and; (ii) a developer component comprising (c) an oxidizing agent. Additionally, the present invention also relates to a method of making a tint component using the pyrazole salt compound of the invention. This and other aspects of the inventions will now be discussed in further details.

DETAILED DESCRIPTION OF THE INVENTION

Definitions

Figure 1:
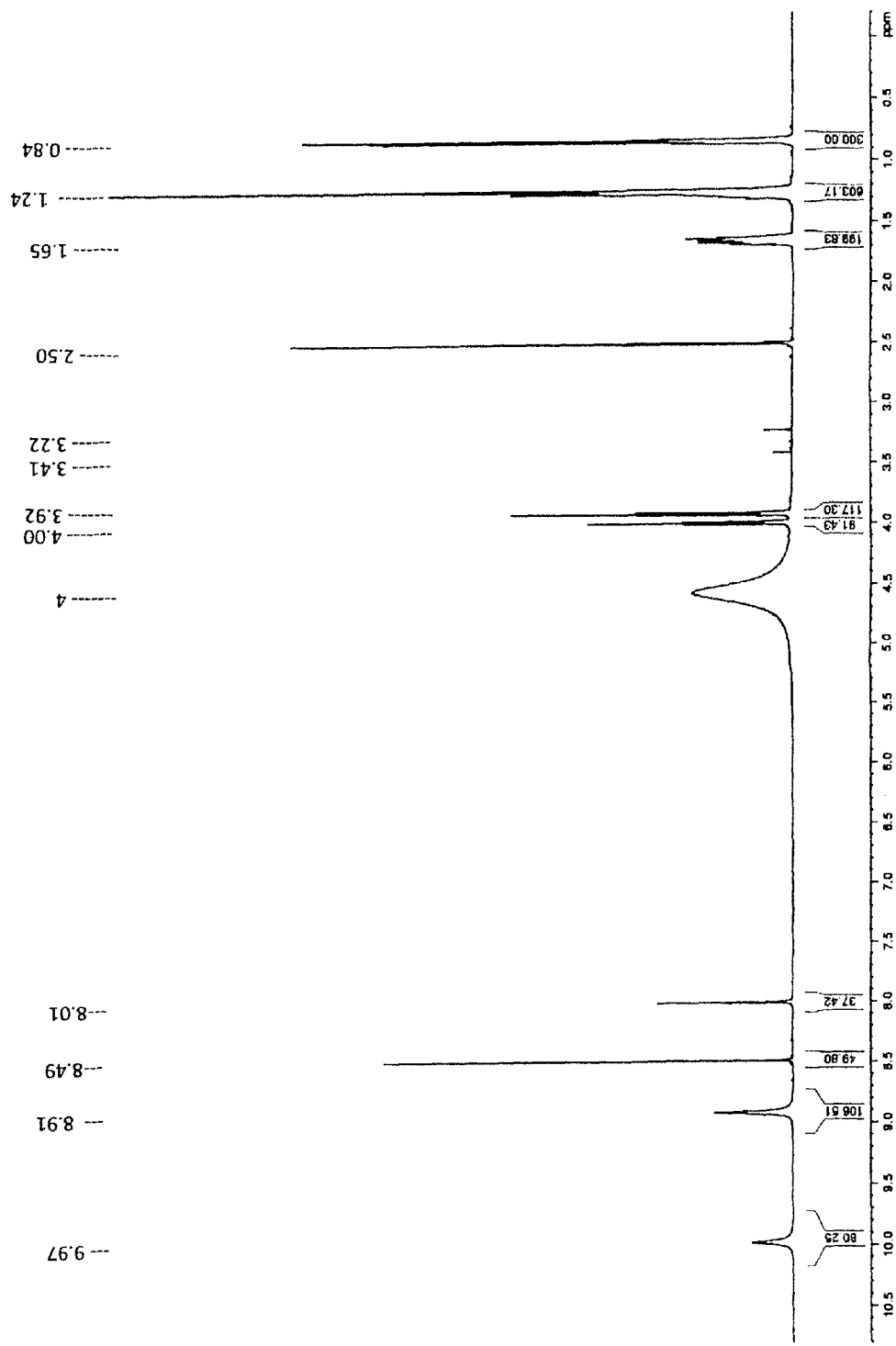
FIG. 1 is $^1$HNMR of 5-amino-4-nitroso-1-n-hexyl-1H-pyrazole HCl salt (herein I-a).

As used herein, the term "composition for the oxidative dyeing of keratin fibers" means a ready-to-use composition in a suitable carrier medium for dyeing keratin fibers, in particular human hair, comprising oxidative dye precursors (primary intermediates and couplers) and an oxidizing agent. These compositions can typically be the result of a mixture of two compositions namely a tint component comprising the dye precursors and usually an alkalizing agent such as ammonia and a developer component comprising the oxidizing agent.

As used herein, the term "keratin" refers to a scleroprotein found in epidermal tissues and modified into hard structures such as horns, hair, and nails. As used herein, the term "hair" refers to keratinous fibers on a living, e.g. a person, or non-living body, e.g. in a wig, hairpiece, or other aggregation of non-living keratinous fibers. Mammalian, preferably human, hair is a preferred. Notably, hair, wool, fur, and other keratinous fibers are suitable substrates for coloring by the compounds and compositions described herein.

As used herein, the term "oxidative hair coloring dye precursors" or more simply "dye precursors" refers to compounds that may be used in the composition to act as primary intermediates, couplers, or both, in order to provide color to keratinous fibers.

It is to be understood that when this development refers to a particular structure, all of the reasonable additional tautomeric structures are included. In the art, tautomeric structures are frequently represented by one single structure and the invention follows this general practice.

Pyrazole Compound

The compound of the invention is the hemisulfate salt of 1-hexyl-1H-pyrazole-4,5-diamine, and can be described according to the general formula (IX-a):

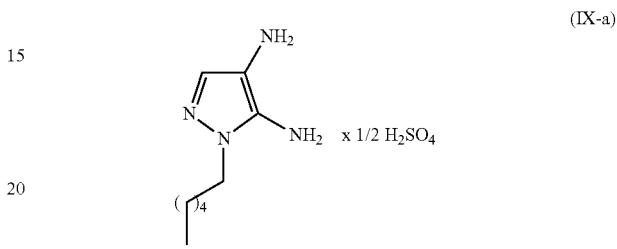

Synthesis 1-hexyl-1H-pyrazole-4,5-diamine hemisulfate may be synthesized using any conventional techniques. For example the process disclosed in U.S. Pat. No. 5,663,366 may be adapted in which instead of using an equimolar amount of sulfuric acid or twice the molar amount of hydrochloric acid, half a molar equivalent sulfuric acid is used to form the pyrazole salt (see in particular U.S. Pat. No. 5,663,366, Production example 11).

Another process comprising a telescoping one-pot reaction leading to intermediate 5-amino-4-nitroso-1-n-hexyl-pyrazole-HCl (I-a), which has been developed by the present inventors and subject of a co-filed application, can be used and comprises the steps of:

(a) synthesizing 3-hydrazinylpropanenitrile (IV)

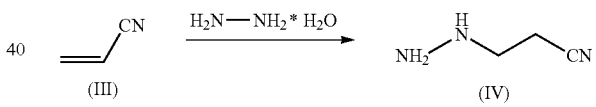

(b) synthesizing 3-(2-hexylidenehydrazinyl)propanenitrile (VI-a)

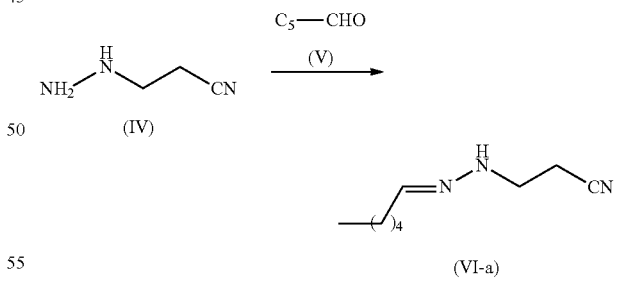

(c) synthesizing 5-amino-1-n-hexyl-1H-pyrazole (VII-a)

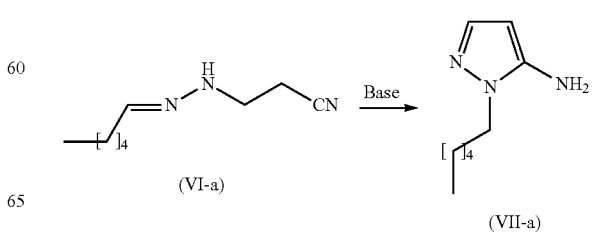

(d) synthesizing 5-amino-4-nitroso-1-n-hexyl-1H-pyrazole-HCl (I-a)

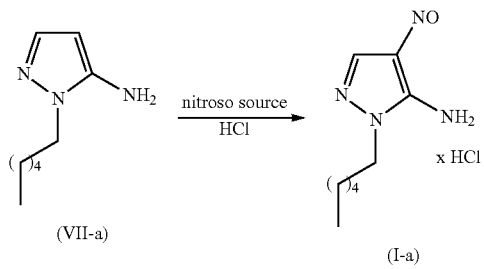

(e) synthesizing 5-amino-4-nitroso-1-n-hexyl-1H-pyrazole base (VIII-a)

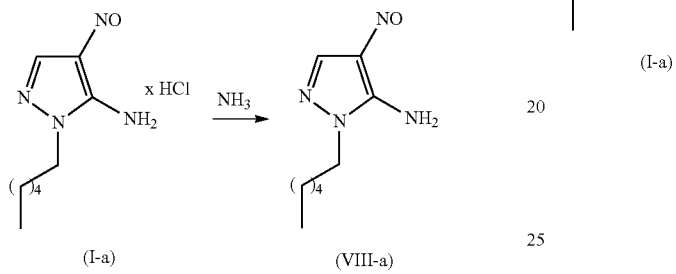

(f) synthesizing 4,5-diamino-1-n-hexyl-1H-pyrazole hemisulfate (IX-a)

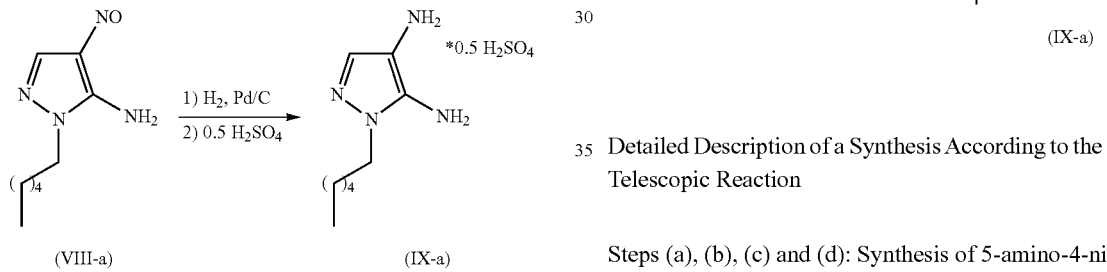

As an alternative to the subsequent reactions (e)+(f), the reaction on compound (I-a) can be:

(g) synthesizing 4,5-diamino-1-n-hexyl-1H-pyrazole hemisulfate (IX-a) from compound (I-a):

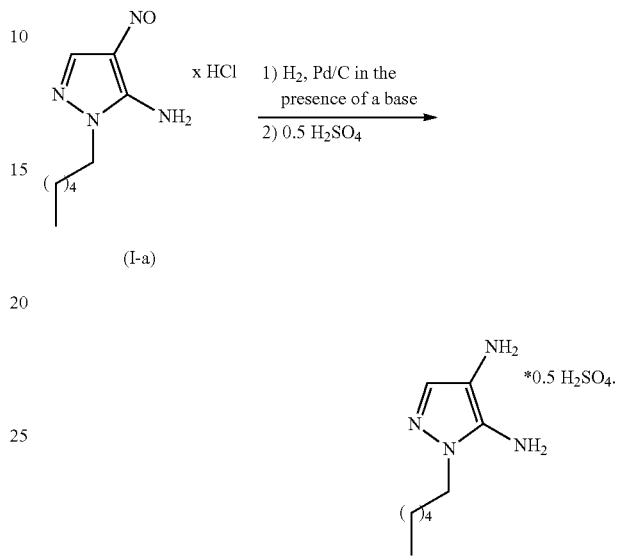

Detailed Description of a Synthesis According to the One Pot Telescopic Reaction Steps (a), (b), (c) and (d): Synthesis of 5-amino-4-nitroso-1-n-hexyl-1H-pyrazole xHCl (I-a)

|       |       |
|-------|-------|
|       | To a 0° C. cold solution of |
| 5.1 kg | hydrazine hydrate diluted with |
| 10.2 l | propyl alcohol are continuously added at approx. 0° C. |
| 5.67 kg | Acrylonitrile was added with control of the temperature. After the addition the reaction mixture is further stirred for a while at 0° C., then heated to room temperature and additionally stirred further for 30 min |
|       | Immediately afterwards |
| 10.7 kg | hexanal are continuously added at room temperature with control of the temperature. |
|       | After finishing the addition of hexanal the reaction mixture is stirred awhile and then reduced to dryness under vacuum. |
|       | The residual liquid residue is diluted one after another with |
| 15.3 l | propyl alcohol and |
| 1.70 l | methanol and then heated to reflux. Under reflux and with intensive stirring a prepared solution of |
| 2.20 kg | sodium methoxide, as 30% solution dissolved in methanol |
| 1.70 l | propyl alcohol is continuously added After the addition the reaction mixture is stirred further for a period of approx. 2 h. Thereafter the solution is cooled down to less than 0° C. and |
| 11.9 kg | 3-methylbutyl nitrite is added under temperature control so that the reaction temperature is kept at less than 0° C. |
|       | After that the cold solution is continuously added into a less than 0° C. cold solution of |
| 25.1 kg | HCl conc. in |
| 57.9 l | 1,2-dimethoxyethane with continuous cooling to keep the reaction temperature at less than 0° C. When finishing the addition the formed suspension is further stirred at less than 0° C. for 0.5 h and then isolated yielding 12.6 kg 5-amino-4-nitroso-1-n-hexyl-1H-pyrazole × HCl (I-a) |

Step (e) Synthesis of 5-amino-4-nitroso-1-n-hexyl-1H-pyrazole (VIII-a)

| | |
|---|---|
| 22.1 kg | 5-amino-4-nitroso-1-n-hexyl-1H-pyrazole × HCl (I-a) are dissolved in |
| 66.3 l | methanol and |
| 49.7 l | water. At room temperature a solution of |
| 7.77 kg | ammonia 25% in |
| 22.1 l | water is added within 0.5 hr. After finishing the addition the formed suspension is cooled down to room temperature. After stirring at room temperature for awhile, the precipitate is isolated yielding 17.0 kg 5-amino-4-nitroso-1-n-hexyl-1H-pyrazole (VIII-a) |

Step (f) Synthesis of 4,5-diamino-1-n-hexyl-1H-pyrazole × 0.5 $H_2SO_4$ (IX-a) (starting with 5-amino-4-nitroso-1-n-hexyl-1H-pyrazole (VIII-a) (free base))

| | |
|---|---|
| | The mixture of |
| 7.0 kg | 5-amino-4-nitroso-1-n-hexyl-1H-pyrazole (VIII-a), |
| 0.07 kg | catalyst Pd/C 10%, containing 50% water, and |
| 1.4 kg | activated carbon, suspended in |
| 21.0 l | ethanol is hydrogenated at 60-80° C. under a pressure of 2-3 bar abs. When the reaction is finished, the solution is cooled to room temperature and filtered. The filter residue is washed twice with |
| 5.6 l | ethanol in each case. The obtained filtrate and the washing liquids are slowly added to a approx. 50° C. warm solution of |
| 2.27 kg | sulfuric acid conc. in |
| 16.8 l | water and |
| 7.0 l | ethanol. The addition is done at 50-55° C. During the addition the desired product precipitates. When the addition is finished the suspension is cooled down to 0-3° C., stirred further for approx. 30 min at the same temperature and filtered yielding 8.26 kg 4,5-diamino-1-n-hexyl-1H-pyrazole × 0.5 $H_2SO_4$ (IX-a) |

Step (g): Synthesis of 4,5-amino-1-n-hexyl-pyrazole hemisulfate—direct reduction of (I-a) to (IX-a) with use of sodium acetate

| | |
|---|---|
| 40.0 g | 5-amino-4-nitroso-1-n-hexyl-1H-pyrazole × HCl (I-a) are suspended in |
| 120 ml | ethanol. With intensive stirring |
| 15.5 g | sodium acetate are continuously added. The suspension was stirred for a while before |
| 0.4 g | catalyst Pd/C 10% are added under an inert atmosphere. Afterwards the reaction mixture is hydrogenated at 50-70° C. under a hydrogen pressure of approx. 3 bar. When the hydrogenation has finished the reaction mixture is filtered. The filter residue is washed twice with |
| 32 ml | ethanol. The filtrate and the washing liquid are continuously added into a warm (50-60° C.) solution of |
| 10.9 g | sulfuric acid conc. in |
| 96 ml | water and |
| 32 ml | ethanol over a period of 30 min After finishing the addition the formed suspension is cooled down to 0-5° C. After stirring at 0-5° C. for a while, the precipitate is isolated yielding 35.4 g 4,5-diamino-1-n-hexyl-1H-pyrazole hemisulfate (IX-a) |

Step (g'): Synthesis of 4,5-amino-1-n-hexyl-1H-pyrazole hemisulfate—direct reduction of (I-a) to (IX-a) with use of triethylamine

| | |
|---|---|
| 30.0 g | 5-amino-4-nitroso-1-n-hexyl-1H-pyrazole × HCl are suspended in |
| 60 ml | ethanol. With intensive stirring |
| 13.7 g | triethylamine are continuously added. The suspension was stirred for a while before |
| 0.3 g | catalyst Pd/C 10%, suspended in |

-continued

| 30 ml | ethanol, are added under an inert atmosphere. |
| | Afterwards the reaction mixture is hydrogenated at 50-70° C. under a hydrogen pressure of approx. 3 bar. |
| | When the hydrogenation has finished the reaction mixture is filtered. The filter residue is washed twice with |
| 22 ml | ethanol. |
| | The filtrate and the washing liquid are continuously added into a warm (50-60° C.) solution of |
| 8.85 g | sulfuric acid conc. in |
| 72 ml | water and |
| 33 ml | ethanol over a period of 30 min. After finishing the addition the formed suspension is cooled down to 0-5° C. After stirring at 0-5° C. for a while, the precipitate is isolated yielding 23.7 g 4,5-diamino-1-n-hexyl-1H-pyrazole hemisulfate (IX-a). |

Figure 2:
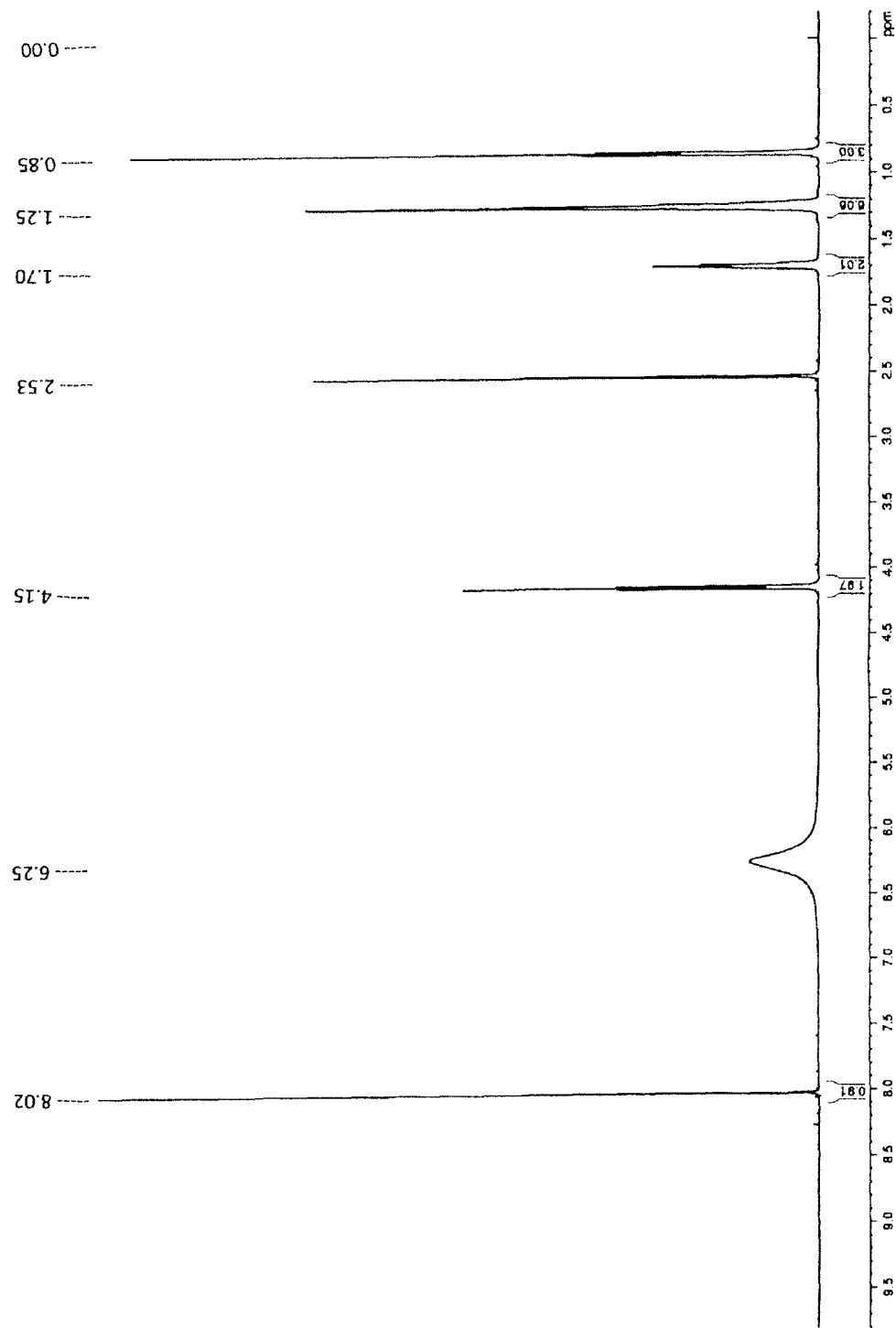
FIG. 2 is $^1$HNMR of 4,5-amino-1-n-hexyl-1H-pyrazole hemisulfate (herein IX-a)

$^1$HNMR spectra of 5-amino-4-nitroso-1-n-hexyl-1H-pyrazole HCl salt (I-a) and of 4,5-amino-1-n-hexyl-1H-pyrazole hemisulfate (herein IX-a) are attached as FIG. 1 and FIG. 2 respectively.

Oxidizing Agent

The compositions for the oxidative dyeing of keratin fibers of the invention comprise an oxidizing agent. A typical suitable oxidizing agents for the oxidative dyeing of keratin fibers is hydrogen peroxide but other oxidizing agents may be used such as, sodium periodate, urea peroxide, melamine peroxide, perborates, percarbonates, perphosphates, persilicates, persulfates, oxidizing enzymes such as uricases, oxidases, and peroxidases, and mixtures thereof. Hydrogen peroxide, perborates, or percarbonates may be preferred.

Another potential oxidizing agent for use herein is a source of peroxymonocarbonate ions. Preferably, such a source is formed in situ from a source of hydrogen peroxide and a hydrogen carbonate ion source. Such an oxidizing agent has been found to be particularly effective at a pH of up to and including 9.5, preferably from about 7.5 to about 9.5 more preferably about pH 9. Moreover, this system is also particularly effective in combination with a source of ammonia or ammonium ions.

Accordingly, any source of these peroxymonocarbonate ions may be utilized. Suitable sources for use herein include sodium, potassium, guanidine, arginine, lithium, calcium, magnesium, barium or ammonium salts of carbonate, carbamate and hydrocarbonate ions and mixtures thereof. In particular, sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof may be preferred. Percarbonate salts may also be utilized to provide both the source of carbonate ions and as an oxidizing agent. Preferred sources of carbonate ions, carbamate and hydrocarbonate ions are sodium hydrogen carbonate, potassium hydrogen carbonate, ammonium carbonate, ammonium carbamate, and mixtures thereof.

The composition for the oxidative dyeing of keratin fibers may usually comprise from about 1% to about 15% by, typically from about 1.5% to about 10% by weight, and more typically from about 2% to about 8% by weight of the oxidizing agent relative to the total weight of the composition.

The oxidizing agent may be provided in a developer component which is mixed to a tint component to obtain the composition of the invention. The developer component may be based on any desired formulation chassis, including any commercial product, for example an oil-in-water emulsion. Typical developer components comprise about 6% or about 9% of the $H_2O_2$ relative to the total weight of the composition. A commercial example is the Welloxon® Emulsion with respectively about 6% and about 9% $H_2O_2$, marketed by Wella and comprising as INCI ingredients: Water, $H_2O_2$, Cetearyl Alcohol, Ceteareth-25, Salicylic Acid, Phosphoric Acid, Disodium Phosphate, Etidronic Acid.

The composition for the oxidative dyeing of keratin fibers of the invention may be formed as thick liquid, cream, gel, emulsion, foam, aerosol mousse or as a solid form to which water is added to generate the oxidant and form a thickened vehicle suitable for hair coloring. They may comprise in addition to the ingredients indicated above further ingredients in order to further enhance the properties of the composition, including but not limited to: solvents; oxidative dyes, direct dyes; oxidizing agents; radical scavengers; thickeners and or rheology modifiers; chelants; pH modifiers and buffering agents; carbonate ion sources; peroxymonocarbonate ion sources; anionic, cationic, nonionic, amphoteric or zwitterionic surfactants, or mixtures thereof; anionic, cationic, nonionic, amphoteric or zwitterionic polymers, or mixtures thereof; fragrances; enzymes; dispersing agents; peroxide stabilizing agents; antioxidants; natural ingredients, e.g. proteins and protein compounds, and plant extracts; conditioning agents including silicones and cationic polymers, ceramides, preserving agents; and opacifiers and pearling agents (such as titanium dioxide and mica). Some adjuvants referred to above, but not specifically described below, which are suitable are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose. A few of these ingredients are discussed hereinbelow, whose disclosure is of course non-exhaustive.

Alkalizing Agent

The composition for the oxidative dyeing of keratin fibers may further comprise, generally in the tint component, an alkalizing agent as known in the art. Any alkalizing agent known in the art may be used such as ammonia, alkanolamines for example monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol, guanidium salts, alkali metal and ammonium hydroxides such as sodium hydroxide, alkali metal and ammonium carbonates, and mixtures thereof. Typical alkalizing agents are ammonia and/or monoethanolamine.

Typically, the compositions for the oxidative dyeing of keratin fibers comprise from about 0.1% to about 10%, preferably from about 0.5% to about 6%, more preferably from about 1% to about 4% by weight of the alkalizing agent relative to the total weight of the composition.

Dye Precursors

In addition to the pyrazole compound of the invention, the compositions for the oxidative dyeing of keratin fibers may comprise further primary intermediates and couplers. When the composition is obtained by mixing a tint component and a developer component, the primary intermediates and couplers may be preferably incorporated in the tint component.

Suitable further primary intermediates for use in hair dyeing compositions include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl) diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, physiologically compatible water-soluble salt thereof and mixtures thereof.

The 1-hexyl-1H-pyrazole-4,5-diamine hemisulfate (I) compound together with other optional primary intermediates is preferably combined with at least one coupler in the composition for dyeing hair. Common couplers are selected form the group consisting of; resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylamino anisole, 1,3-bis-(2,4-diaminophenoxy)-propane, 2,2'-(2-methyl-1,3-phenylene)bis (azanediyl)diethanol, benzene-1,3-diamine, 2,2'-(4,6-diamino-1,3-phenylene)bis(oxy)diethanol, 3-(pyrrolidin-1-yl) aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5 (4H)-one, 1,2,4-trihydroxybenzene, 2-(benzo[d][1,3]dioxol-5-ylamino)ethanol (also known as hydroxyethyl-3,4-methylenedioxyaniline), physiologically compatible water-soluble salt thereof and mixtures thereof.

Typically, the compositions for the oxidative dyeing of keratin fibers comprise from about 0.1% to about 10%, preferably from about 0.3% to about 6%, more preferably from about 0.5% to about 4% by weight of the couplers relative to the total weight of the composition.

Direct Dyes

The hair dyeing compositions of the present invention may also comprise compatible direct dyes, in an amount sufficient to provide additional coloring, particularly with regard to intensity. Typically, such an amount will range from about 0.05% to about 4%, by weight of the direct dyes relative to the total weight of the composition. When the composition is obtained by mixing a tint component and a developer component, the direct dyes are usually incorporated in the tint component.

The following direct dyes are commonly used: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4, Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4-a,9,9a,10-tetrahydroanthracen-1-ylamino)-N-propylpropan-1-aminium bromide, Disperse Dyes such as Disperse Red 17, Disperse Violet 1, Disperse Red 15, Disperse Violet 1, Disperse Black 9, Disperse Blue 3, Disperse Blue 23, Disperse Blue 377, Nitro Dyes such as 1-(2-(4-nitrophenylamino) ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene) bis(azanediyl)diethanol, HC Yellow No. 5, HC Red No. 7, HC Blue No. 2, HC Yellow No. 4, HC Yellow No. 2, HC Orange No. 1, HC Red No. 1,2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9,2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14, and Natural dyes such as Annato, Anthocyanin, Beetroot, Carotene, Capsanthin, Lycopene, Chlorophyll, Henna, Indigo, Cochineal.

Thickeners

The compositions for the oxidative dyeing of keratin fibers of the present invention may comprise a thickener in an amount sufficient to provide the composition with a viscosity so that it can be readily applied to the hair without unduly dripping off the hair and causing mess. Typically, such an amount will be at least 0.05%, preferably at least 0.5%, more preferably at least 1%, by weight of thickener relative to the total weight of the composition. When the composition is obtained by mixing several components, the thickener may be present in any of the components.

Preferred for use herein are salt tolerant thickeners, including but not limited to: xanthan, guar, hydroxypropyl guar, scleroglucan, methyl cellulose, ethyl cellulose (available as AQUACOTE™), hydroxyethyl cellulose (NATROSOL™), carboxymethyl cellulose, hydroxypropylmethyl cellulose, microcrystalline cellulose, hydroxybutylmethyl cellulose, hydroxypropyl cellulose (available as KLUCEL™), hydroxyethyl ethyl cellulose, cetyl hydroxyethyl cellulose (available as NATROSOL™) Plus 330), N-vinylpyrollidone (available as POVIDONE™), Acrylates/Ceteth-20 Itaconate Copolymer (available as STRUCTURE™ 3001), hydroxypropyl starch phosphate (available as STRUCTURE™ ZEA), polyethoxylated urethanes or polycarbamyl polyglycol ester (e.g. PEG-150/Decyl/SMDI copolymer (available as ACULYN™ 44), PEG-150/Stearyl/SMDI copolymer available as ACULYN™ 46), Acrylates/Beheneth-25 Methacrylate Copolymer (available as ACULYN™ 28), Acrylates/Vinyl Neodecanoate Crosspolymer (available as ACULYN™ 38), Acrylates/Steareth-20 Methacrylate Crosspolymer (available as ACULYN™ 88), PEG-150 Distearate (available as ACULYN™ 60), trihydroxystearin (available as THIXCIN™), acrylates copolymer (e.g. available as ACULYN™ 33) or hydrophobically modified acrylate copolymers (e.g. Acrylates/Steareth-20 Methacrylate Copolymer (available as ACULYN™ 22), non-ionic amphophilic polymers comprising at least one fatty chain and at least one hydrophilic unit selected from polyether urethanes comprising at least one fatty chain.

Also preferred for use herein are thickeners based on lamellar gel network systems, comprising at least one surfactant or amphophile having an HLB of 6 or less and a melting point of at least 30° C., preferably selected from fatty alcohols comprising from 14 to 30 carbon atoms, or oxyethylenated fatty alcohols comprising from 16 to 30 carbon atoms and 2 units or less of ethylene oxide, and further comprising at least one ionic or nonionic surfactant, preferably selected from:

- anionic surfactants selected from C8-C30 alkyl sulfates, preferably C12-C18 alkyl sulfates,
- anionic surfactants according to the formula $R_nX_mYM$, wherein R is independently selected from alkyl, alkenyl or alkylaryl groups having from 8 to 30 carbon atoms, X is independently selected from polar groups comprising at least one carbon atom and at least one oxygen or nitrogen atom, Y is an anionic group selected from carboxylates, sulphates, sulphonates or phosphates, n and m are independently 1 or 2, and M is hydrogen or a salt forming cation and mixture thereof, most preferably selected from C8-C30 alkyl ether phosphates having from 1 to 20, preferable 2 to 10 ethylene oxide units (e.g. available as CRODAFOS™ CES);
- non-ionic surfactant comprising one or more polyethyleneoxide chains, preferably each polyethyleneoxide chain has on average at least 50 ethylene oxide units and most preferably 100 to 200 ethylene oxide units (e.g. available as VOLPO™ S200),
- cationic surfactants selected from quaternary ammonium salts or amido-amines having at least one fatty chain, preferably comprising at least 16 carbon atoms and most preferably at least 20 carbon atoms, and mixture thereof.

Examples of such lamellar gel network systems are disclosed in EP1,832,273 and EP2,103,299.

The composition preferably comprises a mixture of cetearyl alcohol and dicetyl phosphate and ceteth-10 phosphate (e.g. available as CRODAFOS™ CES).

Chelants

The compositions of the present invention may comprise chelants in an amount sufficient to reduce the amount of metals available to interact with formulation components, particularly oxidizing agents, more particularly peroxides. Typically, such an amount range from at least 0.15%, preferably at least 0.25% by weight of the chelants relative to the total weight of the composition. Suitable chelants for use herein include but are not limited to: diethylenetriamine-N, N',N''-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, and N,N'-bis(2-hydroxybenzyl)ethylenediamine-N,N'-diacetic acid chelants (preferably EDDS (ethylenediaminedisuccinic acid)), carboxylic acids (preferably aminocarboxylic acids), phosphonic acids (preferably aminophosphonic acids) and polyphosphoric acids (in particular straight polyphosphoric acids), their salts and derivatives. When the composition is obtained by mixing a tint component and a developer component, the chelants may be incorporated in the tint component or in the developer component or in both. A chelant is usually present in developer components for stability reason.

pH Modifiers

The compositions of the present invention may comprise in addition to the alkalizing agent discussed above a pH modifier and/or buffering agent in an amount that is sufficiently effective to adjust the pH of the composition to fall within a range from about 3 to about 13, preferably from about 8 to about 12, more preferably from about 9 to about 11.

Radical Scavengers

According to the present invention, the compositions may comprise a radical scavenger. As used herein the term radical scavenger refers to a species that can react with a radical, to convert the radical species by a series of fast reactions to an unreactive or less reactive species. The radical scavenger is also preferably selected such that it is not an identical species as the alkalizing agent and is present in an amount sufficient to reduce the damage to the hair during the coloring/bleaching process. The compositions of the present invention comprise a radical scavenger from about 0.1% to about 10%, preferably from about 1% to about 7% by weight of the radical scavenger relative to the total weight of the composition Suitable radical scavengers for use herein may be selected from the classes of alkanolamines, amino sugars, amino acids, esters of amino acids and mixtures thereof. Suitable compounds include 3-substituted-pyrazol-5-ones, 3-carboxy-1H-pyrazol-5-one, 3-methyl-1-phenyl-pyrazol-5-one, 3-methyl-1-p-tolyl-pyrazol-5-one, 3-methyl-1-(4-sulfophenyl)-pyrazol-5-one, 3-methyl-1-(4-sulfoamidophenyl)-pyrazol-5-one, 3-methyl-1-(3-sulfophenyl)-pyrazol-5-one, 3-methyl-1-(3-sulfoamidophenyl)-pyrazol-5-one, 3-methyl-1-(2-chloro-5-sulfophenyl)-pyrazol-5-one, 3-methyl-1-(2,5-dichloro-4-sulfophenyl)-pyrazol-5-one, 3-methyl-1-(4-chlorophenyl)-pyrazol-5-one, 3-methyl-1-(4-carboxyphenyl)-pyrazol-5-one, 3-carboxy-1-phenyl-pyrazol-5-one, 3-carboxy-1-(4-sulfophenyl)-pyrazol-5-one, 1,3-diphenyl-pyrazol-5-one, methylpyrazol-5-one-3-carboxylate, 3-amino-1-propanol, 4-amino-1-butanol,5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetyl-glucosamine, glycine, arginine, lysine, proline, glutamine, histidine, sarcosine, serine, glutamic acid, tryptophan, or mixtures thereof, or the salts, such as the potassium, sodium, or ammonium salts thereof, or mixtures thereof. In some embodiments, the inventive compositions may comprise glycine, sarcosine, lysine, serine, 2-methoxyethylamine, glucosamine, glutamic acid, morpholine, piperidine, ethylamine, 3-amino-1-propanol, or mixtures thereof.

Method of Hair Dyeing

In order to use the dyeing composition, the tint component and developer components are usually mixed immediately prior to use and a sufficient amount of the mixture is applied to the hair, according to the hair abundance, generally from about 60 to about 250 grams. Upon such preparation the composition is applied to the hair to be dyed and remains in contact with the hair for an amount of time effective to dye the hair. Typically, the hair dye composition is allowed to act on the hair from about 2 to about 60, preferably about 15 to about 45, more preferably about 30 minutes, at a temperature ranging from 15° C. to about 50° C. Thereafter, the hair is rinsed with water to remove the composition and dried. If necessary, the hair is washed with a shampoo and rinsed, e.g., with water or a weakly acidic solution, such as a citric acid or tartaric acid solution, and dried. Optionally, a separate conditioning product may also be provided.

The method of dyeing hair with the composition may therefore comprise the steps of:

(i) providing a tint component comprising (a) 1-hexyl-1H-pyrazole-4,5-diamine hemisulfate of formula (I); (b) a coupler as defined above;

(ii) providing a developer component comprising (c) an oxidizing agent;

(iii) mixing the tint component and the developer component to obtain a composition for the oxidative dyeing of keratin fibers according to the composition of the invention;

(iv) applying said composition for the oxidative dyeing of keratin fibers onto the hair.

The method may further comprise waiting a period of time, typically between 2 minutes and 60 minutes, and then rinsing the composition from the hair.

The compositions can be applied on hair via applicator bottle or brush. It can be used on full head or partly on single strands (highlight application) as common highlight applicator foils, caps and special applicators can be used, but also freehand techniques such as balayage, with brush and/or combs can be possible. The composition can also be applied as a mousse via a manual spray, a pressurized container or an aerosol mousse.

The composition may be dispensed as a solid form to which water is added to generate the oxidant and form a thickened vehicle suitable for hair coloring.

The dye combination of the invention may also be used in three components system. See for example disclosed US2010/0223739A2 assigned to L'Oreal. Such a process and kit for lightening or dyeing keratin fibers may comprise the following composition applied to the hair fibers: an aqueous cosmetic composition (A) comprising at least one fatty substance and at least one surfactant; a cosmetic composition (B) comprising at least one alkaline agent and the oxidative dyes of the invention and if present direct dyes and other oxidative dyes, a cosmetic composition (C) comprising at least one oxidizing agent, wherein the amount of the at least one fatty substance in composition (A) is greater than 20% by weight relative to the total weight of composition (A).

Methods of Making—Kit

The composition, and its tint component and developer component, may be manufactured by conventional processes known in the art for manufacturing oxidative dyeing products, and admixing the ingredients of each component composition in suitable vessels, followed by packaging in appropriate individual containers. The components may be for example packaged in plastic or aluminum bottles.

The present invention also relates to a method of making a hair dye composition comprise the steps of:

(i) providing a tint component comprising (a) 1-hexyl-1H-pyrazole-4,5-diamine hemisulfate and (b) a coupler as defined above;

(ii) providing a developer component comprising (c) an oxidizing agent;

(iii) mixing the tint component and the developer component to obtain a composition for the oxidative dyeing of keratin fibers according to the composition of the invention.

In particular, the present invention may be provided as a kit comprising different components to be mixed by the consumer or salon stylist to obtain a hair dyeing composition according to the invention. Such a kit may comprise:

(i) a tint component comprising (a) 1-hexyl-1H-pyrazole-4,5-diamine hemisulfate, and (b) a coupler; and ii) a developer component comprising an oxidizing agent.

The kit may be presented in a single package comprising separate containers for the tint component, the developer component, and optionally a conditioner, a color refresher or other hair treatment product, instructions for use, gloves. The instructions for use include the steps of the method described above and optionally provide visual cues or pictures for the desired steps of the method. Kits are usually sold in retail products with enough material in each component for preparing a hair dyeing composition for one use.

The composition may be dispensed as a foam using for example manually-actuable, non-aerosol dispenser such as a pump or squeeze foamers, aerosol mousse. See for example EP 613,728 B1, WO 97/013585 A1, EP 1,716,933A1, U.S. Pat. Nos. 3,709,437, 3,937,364, 4,022,351, 4,147,306, 4,184,615, 4,615,467 and FR 2,604,622. One particular example of a squeeze foamer useful herein is able to dispense from an upright or inverted position such as the one discussed in U.S. Pat. No. 6,604,693 assigned to Taplast, and more specifically, at column 2, line 65, through column 4, line 67 of that patent.

The composition may be dispensed as a solid form to which water is added to generate the oxidant and form a thickened vehicle suitable for hair coloring.

EXAMPLES

The following are non-limiting examples of the compositions of the present invention. The examples are given solely for the purpose of illustration and are not to be construed as limitations of the present invention, as many variations thereof are possible without departing from the spirit and scope of the invention, which would be recognized by one of ordinary skill in the art.

Stability

Experimental Protocol:

1) Sample Preparation:

As summarized in the table below, three 1-hexyl-1H-pyrazole-4,5-diamine salts were synthesized through precipitation of the free base in presence of the corresponding acids and purification to obtain the hemisulfate, sulfate and dihydrochloride salts. Each sample was then placed on paper.

2) HPLC Measurement:

In order to measure and compare the stability of the three different salts, a small amount of each sample was taken at four different time points and an HPLC analysis was conducted in order to measure the formation of the undesired dimer of formula (II).

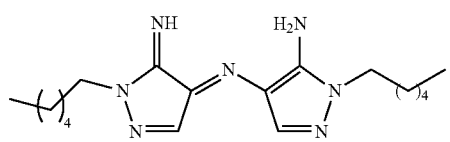

3) Storage Conditions:

TABLE 1

Storage conditions of the samples and time of measurement

| Storage conditions | Time point $t_0$ | For each compound, a sample of about 1.5 g was spread on a filter paper. |
| --- | --- | --- |
| | Time point $t_1$ | The samples were stored during this period in a closed, dark storage room with temperature at 21° C. under controlled humidity conditions. At this point, 23 days from beginning of the experiment passed. |
| | Time point $t_2$ | After 23 days in the dark storage room the samples were stored 3 more days without light protection under a lab hood at room temperature. During this time, the weather was rainy, so that the air humidity was relatively higher than normal. At this point, 26 days from beginning of experiment passed. |

TABLE 1-continued

Storage conditions of the samples and time of measurement

| | Time point $t_3$ | After 26 days, the samples were stored 5 extra days under the same conditions as before, with the weather conditions being mostly pleasant. At this point, 31 days from beginning of experiment passed |
| --- | --- | --- |

3) Results:

TABLE 2

Stability results

| | Amount of dimers at the time point: | | | |
| --- | --- | --- | --- | --- |
| C6-Pyrazole salts | $t_0$ | $t_1$ | $t_2$ | $t_3$ |
| C6-Pyrazole × 2 HCl | 45 ppm | 511 ppm | 772 ppm | 1323 ppm |
| C6-Pyrazole sulfate | 11 ppm | 461 ppm | 726 ppm | 1083 ppm |
| C6-Pyrazole hemisulfate | 6 ppm | 37 ppm | 43 ppm | 74 ppm |

Table 2 demonstrates that the hemisulfate salt is more stable than its corresponding sulfate and dihydrochloride salts under the conditions of storage described in table 1. The rate of formation of the dimer impurity is much lower for the hemisulfate than its comparable salts.

Color Intensity

The hair dyeing compositions tested were formulated by mixing a tint component according to the formulation below with a developer component in a 1:1 ratio. The developer component is a commercially available Welloxon developer at 6% (20 vol) peroxide concentration. In all the tests, white hair was used (1.5 g tresses). 3 g tint component+3 g developer component were applied for each switch for 30 minutes at 30° C. The tresses were rinsed for 2 minutes including 30 seconds shampoo.

TABLE 3

Tint Component Formulation

| Ingredients | Weight % |
| --- | --- |
| Ethylenediaminetetraacetic acid disodium salt dihydrate | 0.30% |
| Ascorbic acid | 0.30% |
| Sodium sulfite | 0.4% |
| Laurylethersulfate-28% | 10% |
| Ethanol | 7.85% |
| Each dye precursors (see table 4) | 0.025M |
| Ammonia-25% | 9.10 |
| Water up to | 100% |

The tint component indicated above is formulated with 1-hexyl-1H-pyrazole-4,5-diamine hemisulfate, 1-(4-methylbenzyl)-1H-pyrazole-4,5-diamine hemisulfate and 1-octyl-1H-pyrazole-4,5-diamine hemisulfate combined with five different couplers as defined in the table below. After mixing with the developer component, the resulting mixture was applied to white hair and rinsed. The resulting color shade and its intensity was then assessed by a specially trained assessor. The results are compiled in the Table below. A (−) sign indicates that the intensity was slightly, but significantly, less than the reference C6-pyrazole derivative.

TABLE 4

Colour intensity results

| Coupler → Primary intermediate ↓ | Resorcinol (OH, OH) | 2,4-diamino-phenoxyethanol | 4-amino-2-hydroxy-toluene | 1-Naphtol | 2-amino-4-hydroxyethyl-aminoanisole sulfate |
|---|---|---|---|---|---|
| (IX-a) pyrazole-4,5-diamine with n-hexyl, × 1/2 H₂SO₄ | Pink | Purple | Orange | Purple | Purple |
| pyrazole-4,5-diamine with 4-methylbenzyl, 1/2 H₂SO₄ | Pink (−) | Purple (−) | Orange (−) | Purple (−) | Purple (−) |
| pyrazole-4,5-diamine with n-octyl, 1/2 H₂SO₄ | Pink (−) | Purple (−) | Orange (−) | Purple (−) | Purple (−) |

Table 4 demonstrates that hair tresses dyed with 1-(4-methylbenzyl)-1H-pyrazole-4,5-diamine hemisulfate and 1-octyl-1H-pyrazole-4,5-diamine hemisulfate provide a slightly less intense shade compared to 1-hexyl-1H-pyrazole-4,5-diamine hemisulfate of formula (I) across a range of standard couplers. The colour intensity of the hair tresses dyed with 1-hexyl-1H-pyrazole-4,5-diamine hemisulfate is significantly higher compared to the other 4,5-diaminopyrazoles salts.

Concluding Remark

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All concentrations are listed as weight percent of the dyeing composition, unless otherwise specified.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for imparting improved color intensity as a result of dyeing human keratin fibers, the method comprising applying to human keratin fibers a composition comprising 1-hexyl-1H-pyrazole-4,5-diamine hemisulfate.

2. The method of claim 1 wherein 1-hexyl-1H-pyrazole-4,5-diamine hemisulfate is a primary intermediate.

3. The method of claim 2, wherein the composition further comprises one or more couplers selected from the group consisting of: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), physiologically compatible water-soluble salts thereof and mixtures thereof.

4. The method of claim 2, wherein the composition further comprises one or more additional primary intermediates selected from the group consisting of: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl) diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-*a*]pyrazol-1(5H)-one dimethosulfonate, physiologically compatible water-soluble salts thereof, and mixtures thereof.

\* \* \* \* \*